(12) United States Patent
Pedrazzini

(10) Patent No.: US 11,841,375 B2
(45) Date of Patent: Dec. 12, 2023

(54) AUTOMATION APPARATUS OF ANALYSIS LABORATORY

(71) Applicant: Inpeco Holding Ltd., Qormi (MT)

(72) Inventor: Gianandrea Pedrazzini, Paradiso (CH)

(73) Assignee: Inpeco Holding Ltd., Qormi (MT)

(*) Notice: Subject to any disclaimer, the term of this patent is extended or adjusted under 35 U.S.C. 154(b) by 319 days.

(21) Appl. No.: 17/120,357

(22) Filed: Dec. 14, 2020

(65) Prior Publication Data
US 2021/0190805 A1    Jun. 24, 2021

(30) Foreign Application Priority Data

Dec. 18, 2019    (IT) .................. 102019000024574

(51) Int. Cl.
| | | |
|---|---|---|
| *G01N 35/04* | (2006.01) | |
| *G01N 1/20* | (2006.01) | |
| *G01N 33/487* | (2006.01) | |

(52) U.S. Cl.
CPC .............. *G01N 35/04* (2013.01); *G01N 1/20* (2013.01); *G01N 33/487* (2013.01); *G01N 2001/2028* (2013.01); *G01N 2035/0484* (2013.01)

(58) Field of Classification Search
CPC ........ G01N 35/04; G01N 1/20; G01N 33/487; G01N 2001/2028; G01N 2035/0484; G01N 2035/0406; G01N 2035/0425; G01N 35/021; G01N 2035/0465; G01N 2035/0427; B65G 47/57; B65G 47/643; B65G 2201/0261; B65G 47/682; B65G 47/715; B65G 37/00
See application file for complete search history.

(56) References Cited

FOREIGN PATENT DOCUMENTS

| | | | |
|---|---|---|---|
| EP | 2780724 | B1 | 3/2016 |
| EP | 3060501 | A1 | 8/2016 |
| EP | 3196652 | A1 | 7/2017 |
| EP | 3129791 | B1 | 7/2018 |
| JP | 2019194578 | A | 11/2019 |
| WO | WO-8706709 | A * 11/1987 | ............... B67B 7/02 |
| WO | 2015059620 | A1 | 4/2015 |

OTHER PUBLICATIONS

Itoh, Teruaki, Fully automatic apparatus for pulling out test tube stoppers, WIPO PCT machine translation via google patents (Year: 1987).*
Italian Search Report dated Aug. 19, 2020. 2 pages.

* cited by examiner

*Primary Examiner* — Jennifer Wecker
*Assistant Examiner* — Ali Husain Faraz
(74) *Attorney, Agent, or Firm* — RMCK Law Group PLC

(57) ABSTRACT

An automation apparatus of an analysis laboratory, for handling support devices able to support containers of biological samples. The automation apparatus includes two main automatic belt conveyors arranged in positions spaced from one another on a floor, and at least one auxiliary automatic belt conveyor. The auxiliary belt conveyor is spaced at a different height with respect to the main conveyors, and is operatively connected to the main conveyors by means of lift devices.

12 Claims, 13 Drawing Sheets

AUTOMATION APPARATUS OF ANALYSIS LABORATORY

CROSS-REFERENCE TO RELATED APPLICATION

This application claims priority to Italian Patent Application No. 102019000024574 filed Dec. 18, 2019. The disclosure of the above application is incorporated herein by reference in its entirety.

FIELD OF THE INVENTION

The present invention relates to an automation apparatus of analysis laboratory, for handling support devices provided for supporting containers of biological samples.

PRIOR ART

In the field of laboratory analysis of biological samples, it is widely known the use of automation systems including automatic belt conveyors for transferring biological samples, in suitable containers supported by transport devices, along the laboratory.

The increasing need of having different clinical specialties within a single laboratory, and consequently different types of pre-analysis, analysis, or post-analysis modules, is accompanied by the construction of automation systems of increasingly large dimensions, in terms of length of the belt section, in order to include the greatest number of such modules in the available space.

Problems arise because the automation systems and the related belt conveyors are therefore occupying an increasingly large area in the laboratory, up to constitute a significant physical obstacle for the path of the operators working within the laboratory.

Furthermore, the complexity and the length often reached by an automation system cause that a biological sample, if it has to deal with two consecutive processings by two modules positioned very far from each other in the laboratory, can unnecessarily take a lot of time in circulation along the automation system, in order to cover the significant distance between the two modules.

In the European Patent Application EP 3060501 A1, Applicant proposed an apparatus for the transfer of biological material samples, between laboratory automation systems placed at different heights.

The present invention is based on the desire to propose an automation apparatus of analysis laboratory that overcomes different operational limits present in the apparatus previously proposed by the Applicant.

Object of the Invention

The object of the present invention is to devise an apparatus that allows to eliminate part of the traffic of biological samples in circulation from the ground level, in order to have less area occupation on the laboratory floor and to create passage areas to ensure without problems the transit on foot of laboratory operators and eventually that of other materials useful in the laboratory, transported by the operators themselves or not.

A further object is to eliminate part of the traffic of biological samples in circulation from the ground level, without affecting the flow of biological samples that can be handled by an automation apparatus placed entirely on a floor area.

A further object is to allow biological samples to shorten their path in the laboratory, allowing a more rapid connection between processing modules which are distant from each other.

Another object is to obtain a solution that can be applied indifferently to a single automation system, by quickly connecting two distinct parts thereof, but also to two or more different automation systems, and therefore to two or more different conveyors, present in the same laboratory.

In particular, an object of the transfer of samples between different automation systems is to remedy any failure, replacements, maintenance, states of temporary non-operation of a pre- or post-analysis module or of an analyzer in the starting automation system (while the same module or analyzer is on the contrary working in the destination automation system), or the presence of a specific module present in only one of these automation systems.

Another object is to have a modular solution, scalable both in height and width and which therefore can be in general adapted to different throughputs and to laboratories of different sizes. In particular, the solution must be identically configurable according to the needs, both for a development towards the laboratory ceiling and, alternatively, below the level of the laboratory floor.

SUMMARY OF THE INVENTION

In order to achieve one or more of the aforesaid objects, the invention relates to an automation apparatus of analysis laboratory, for handling support devices provided for supporting containers of biological samples, said automation apparatus comprising:

two main automatic belt conveyors arranged in positions spaced from one another on a floor, and having at least one respective main guide lane on which the support devices can run, at least two lift devices, each associated with a respective main conveyor and each including a bearing structure spaced in a substantially vertical direction, and a movable platform carried by said bearing structure and arranged movable along said bearing structure, at least two main loading/unloading stations, each associated with a respective main conveyor and with its lift device thereof, each main station being able to form and temporarily host batches of said support devices coming from the respective main guide lane, said batches being formed to be transferred to the respective movable platform, or vice versa, at least one auxiliary automatic belt conveyor having at least one auxiliary transport lane, on which the support devices can run, said auxiliary automatic conveyor being operatively connected to the main conveyors by means of the lift devices, and being spaced at a different height with respect to said main conveyors, so that said auxiliary automatic conveyor allows a transport flow of the support devices from one main automatic conveyor to the other main automatic conveyor and/or vice versa, while the space between the main automatic conveyors allows the passage of operators from one side to the other of the main automatic conveyors, at least a pair of auxiliary loading/unloading stations located at the same height as the auxiliary automatic conveyor, each auxiliary station being associated with a respective lift device and being configured to form and host batches of said support devices coming from the auxiliary lane, said batches being formed to be transferred to the respective movable platform, or vice versa, each main and auxiliary station including respective handling elements configured to form batches of support devices and to carry out a loading step of said batches on the movable platform and/or an unloading step of said batches from the movable platform, said automation apparatus further comprising at least one central electronic control unit able to control the handling operations of the support devices along the main and auxiliary conveyors.

According to one or more embodiments, each station comprises a loading bay and an unloading bay, arranged on two opposite sides of the respective movable platform, said loading and unloading bays including, respectively, a set of said handling elements.

According to one or more embodiments, the handling elements of each loading bay include a first pusher element able to form batches of support devices coming from a respective interfacing lane and to move said batches on the respective movable platform. The first pusher element being further able to repeat the shift operation for following rows until filling the loading bay, and to move a batch of support devices formed as a result of the shift of multiple rows, from the loading bay to the movable platform.

Preferably, said first pusher element includes a support structure to which a horizontal bar element is connected which extends transversely along the width of the loading bay, said support structure being mounted sliding along respective guides spaced along one side of the loading bay, and said bar element being mounted vertically sliding along the support structure.

Preferably, each movable platform includes along its adjacent sides, respectively at the loading bays and at the unloading bays, respective movable connecting bridges, able to create a continuous plane between the bays and the movable platform when the movable platform reaches the level of a main or auxiliary station, and to create containment walls during the steps of ascent and descent of the movable platform along the bearing structures of the lift devices.

According to one or more embodiments, the handling elements of the unloading bays include a second pusher element able to move a batch of support devices from the movable platform to the main/auxiliary lane, temporarily passing through an unloading bay.

The invention also relates to an automation system including a plurality of apparatuses according to the features previously indicated, said apparatuses being operatively connected to each other.

BRIEF DESCRIPTION OF THE DRAWINGS

Further features and advantages of the invention will become apparent from the following description with reference to the attached drawings, given purely by way of non-limiting example, in which.

DETAILED DESCRIPTION OF THE INVENTION

The following description illustrates various specific details aimed at an in-depth understanding of examples of one or more embodiments. The embodiments can be made without one or more of the specific details, or with other methods, components, materials, etc. In other cases, known structures and materials or operations are not shown or described in detail to avoid obscuring the various aspects of the embodiments.

Reference to "an embodiment" within this description means that a particular configuration, structure or feature described in relation to the embodiment is included in at least one embodiment. Hence, phrases such as "in an embodiment", possibly present in different places of this description, are not necessarily referred to the same embodiment. Furthermore, particular conformations, structures or characteristics can be combined in an adequate way in one or more embodiments and/or associated with the embodiments in a different way from as illustrated here, whereby for example a characteristic here shown in relation to a figure can be applied to one or more embodiments shown in a different figure.

The references illustrated here are for convenience only and therefore do not limit the field of protection or the scope of the embodiments.

Figure 1:
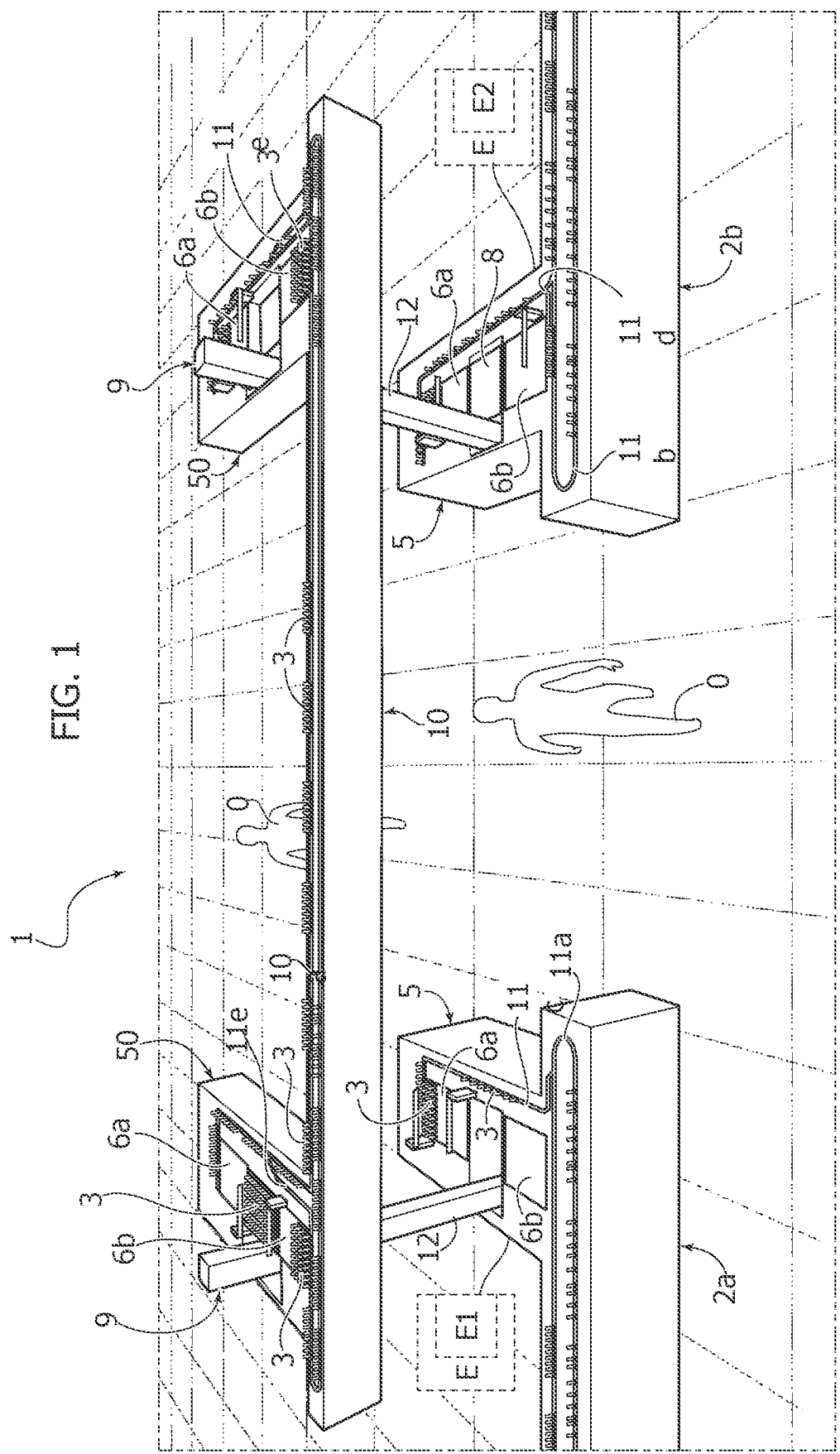
FIG. 1 is a perspective view of an automation apparatus of analysis laboratory, according to a preferred embodiment of the invention.
Figure 13:
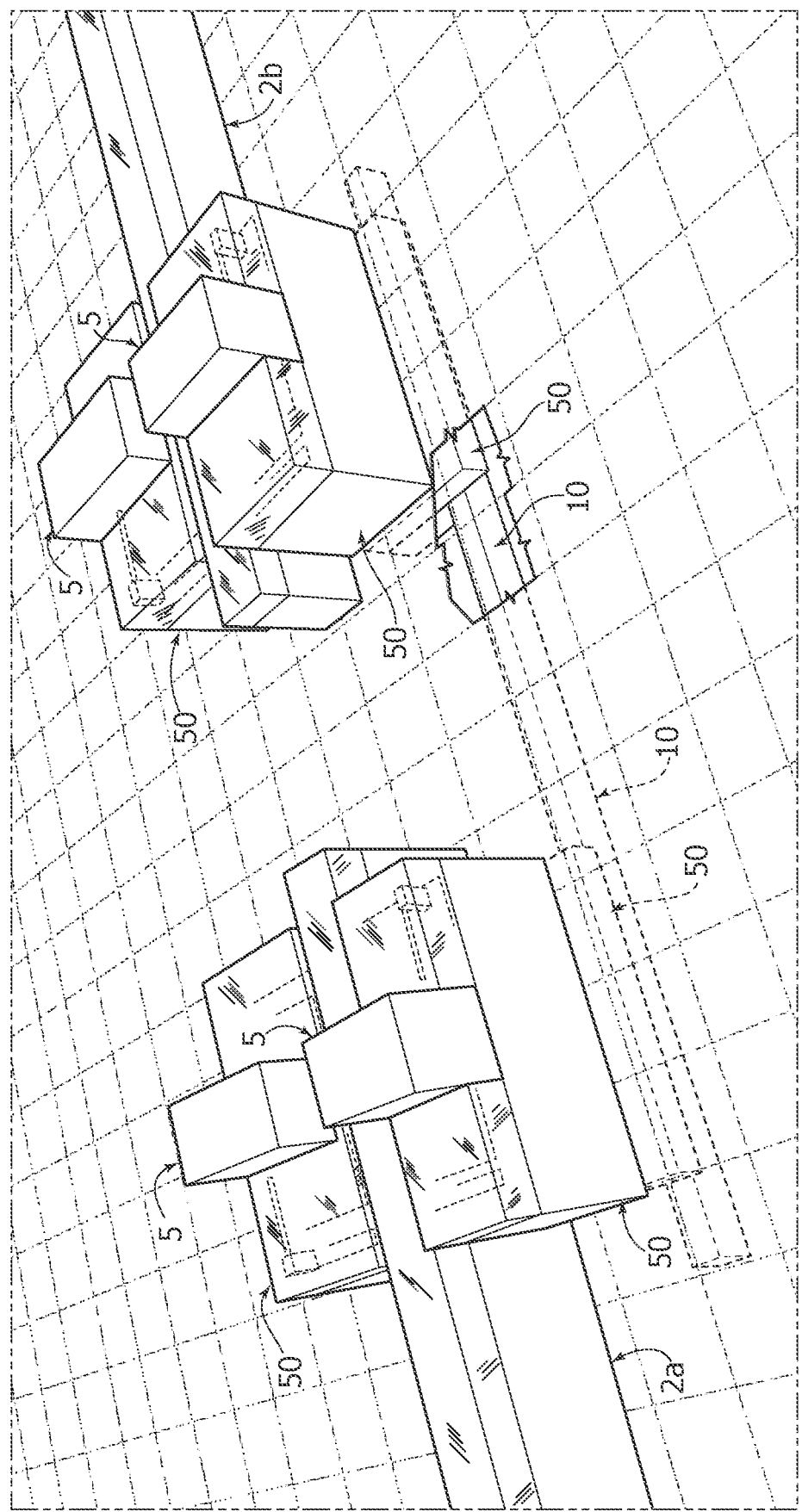

In FIG. 1, reference 1 generally indicates a preferred embodiment of an automation apparatus of analysis laboratory according to the invention. The apparatus 1 is configured to carry a multitude of support devices 4 able to support containers of biological samples 3. More particularly, in the embodiment illustrated in FIG. 1, which will be described in greater detail below, it is clearly shown an apparatus for the overhead transfer of the support devices 4. FIG. 13 instead illustrates an alternative embodiment, which provides for an apparatus 1 arranged for the underground transfer of the support devices 4. This embodiment will not be further explored below, since its inventive concept remains identical with respect to the embodiment illustrated in FIG. 1.

In the preferred embodiment shown in FIG. 1, the automation apparatus 1 has a specular structure which comprises at its ends two main automatic belt conveyors 2a, 2b, which may or may not be connected together to form a single continuous line of automation. In particular, if the two main automatic conveyors 2a, 2b form a single continuous automation line, the connection between the two conveyors takes place at any point of the automation system that occupies the surface of the laboratory (not shown in FIG. 1).

As shown in the perspective view of FIG. 1, the two main automatic belt conveyors 2a, 2b are arranged in mutually spaced positions on a floor, and have at least one respective main guide lane 11a, 11b, on which the support devices 4 can pass. In the specific example illustrated in FIG. 1, each main automatic belt conveyor 2a, 2b has a pair of main lanes 11a, 11b, so as to be able to provide a bidirectional traffic of the support devices 4.

The support devices 4 are configured to stably house a respective biological sample container 3, typically in the form of a test tube. The support devices can be made in accordance with what is described in the European patent EP 3129791 B1 by the Applicant.

According to a technique known in itself, the two main automatic conveyors 2a, 2b are connected, along their extension, to one or more processing or analysis modules, variously distributed along the laboratory (not illustrated in the drawings). It will be therefore appreciated that the two main automatic conveyors 2a, 2b are able to transport the containers of biological samples 3 from/to these processing or analysis modules, in order to complete the planned activities in accordance with a laboratory protocol.

According to a first important feature of the invention, the two main conveyors 2a, 2b include a respective main loading/unloading station 5 of support devices 4. In the embodiment shown in FIG. 1, each main station 5 is arranged in correspondence of one end of the respective main conveyor 2a, 2b.

Each main station 5 is configured to form and temporarily host batches of support devices 4 coming from the main lanes 11a, 11b of the respective main conveyor 2a, 2b. More specifically, the main stations 5 receive a series of support devices 4 which travel along respective interfacing lanes 11c, 11d, which connect the main lanes 11a, 11 b to the stations 5. These main loading/unloading stations 5 are described in more detail in the following description.

According to an essential feature of the invention, the automation apparatus 1 also comprises at least two lift devices 9, each associated with a respective main conveyor 2a, 2b. Each lift device 9 includes a bearing structure 12 spaced along a substantially vertical direction, and a movable platform 8 carried by the bearing structure 12 and arranged movable along the bearing structure 12 both upwards and downwards.

As shown in FIG. 1, each main loading/unloading station 5, besides being associated with a respective main conveyor 2a, 2b, is also associated with one of the lift devices 9, so as to be able to transfer, to the respective movable platform 8, a batch of support devices 4 coming from the interfacing lane 11c, 11d, or a batch of support devices 4 from the movable platform 8 to the main lanes 11a, 11b.

According to a further essential feature of the invention, the automation apparatus 1 further includes at least one auxiliary automatic belt conveyor 10 which is spaced at a different height with respect to the main conveyors 2a, 2b, and is operatively connected to them by means of the lift devices 9. The auxiliary automatic conveyor 10 has at least one auxiliary transport lane 10a on which the support devices 4 can pass. It will be therefore appreciated that the auxiliary conveyor 10 allows a transport flow of the support devices 4 from a main automatic conveyor 2a to the other main automatic conveyor 2b and/or vice versa, while the space between the main automatic conveyors 2a, 2b allows the passage of the operators, indicated with the reference O in FIG. 1, from one side to the other of the main automatic conveyors 2a, 2b.

The automation apparatus 1 also includes a pair of auxiliary loading/unloading stations 50 located at the same height as the auxiliary automatic conveyor 10. Each auxiliary station 50 is associated with a respective lift device 9 and is configured to form and temporarily host batches of support devices 4 coming from the auxiliary lane 10a and to be transferred to the respective movable platform 8, or vice versa. The auxiliary lane 10a is connected to the stations 50 by means of respective interfacing lanes 11e. Each auxiliary station 50 is operatively in communication with the respective main station 5, by means of the respective lift device 9 (and of the relative movable platform 8). It will be therefore appreciated that, to achieve such operational communication, each auxiliary station 50 is vertically aligned with the respective main station 5.

Figure 2:
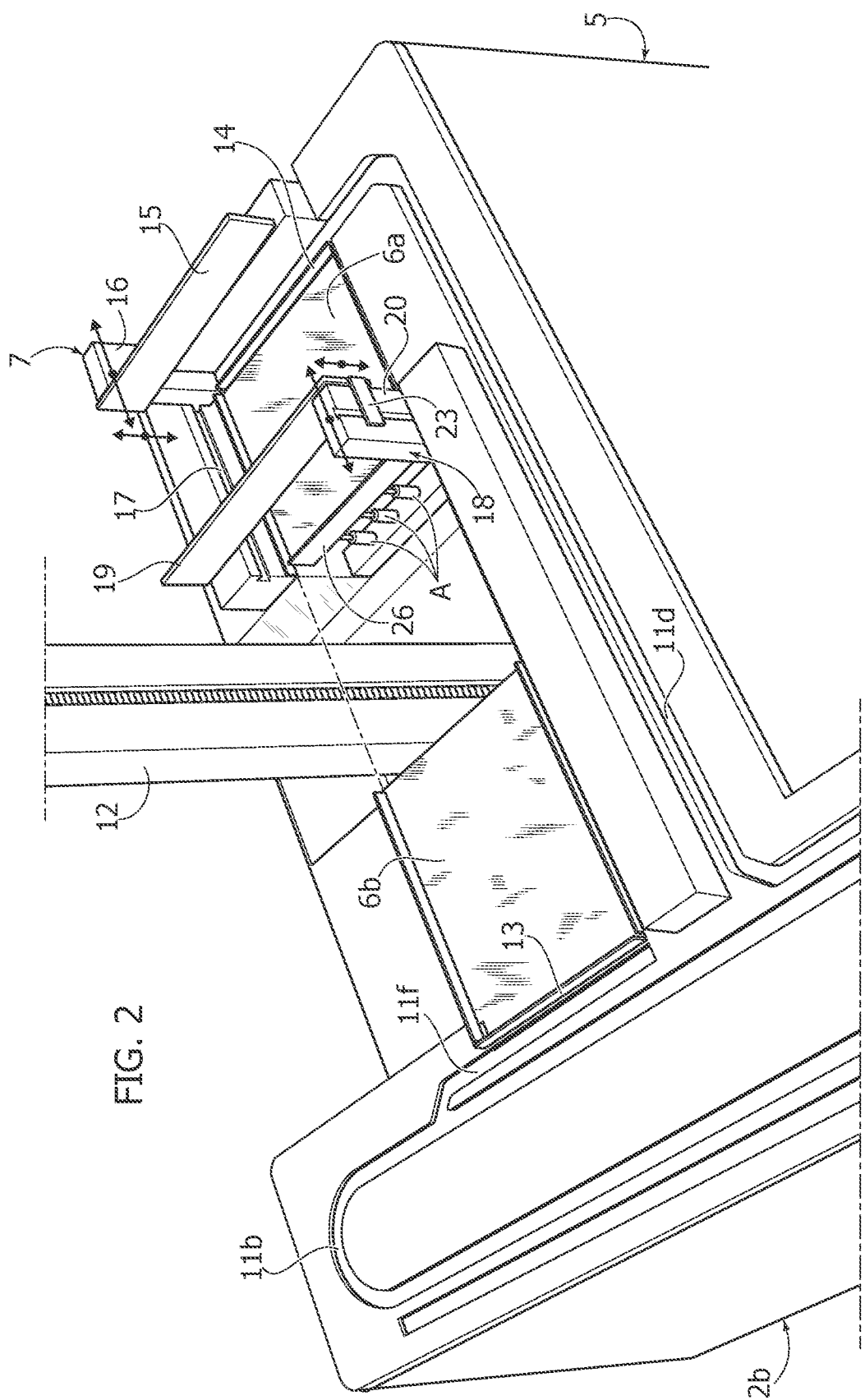
FIG. 2 is an enlarged perspective view of a loading/unloading station illustrated in FIG. 1, FIGS. 3-10 are perspective views illustrating a sequence of operational steps, carried out by the automation apparatus of analysis laboratory according to the invention.

FIG. 2 is a schematic perspective view showing in detail a main station 5. Each main station 5 comprises a loading bay 6a and an unloading bay 6b, arranged at two opposite sides of the respective movable platform 8 (when this is on the same plane as the main station 5). More specifically, the loading bay 6a is able to accommodate a multitude of support devices 4 coming from the main conveyor 2a or 2b, while the unloading bay 6b, at the other end of the movable platform 8, is able to reintroduce the support devices 4 along the main conveyor 2a or 2b.

As previously indicated, between the two bays 6a, 6b, each main station 5 comprises a space within which the movable platform 8 can be arranged so as to create a continuous plane defined by the platform 8 and the bays 6a, 6b. The movable platform 8, connected to a respective vertical shaft lift device 9, bidirectionally transports the support devices 4 accumulated on the platform 8 from/to an auxiliary station 50, identical to the main station 5, but located at a different height with respect to the height of the main conveyor 2a, 2b. The movable platform 8 can be connected to the bearing structure 12, by means of transmission elements, such as for instance a closed loop belt (not shown in the drawings).

Since the auxiliary stations 50 are almost identical to the main stations 5, it will be therefore appreciated that the auxiliary stations 50 are also made with the loading and unloading bays 6a, 6b above indicated.

Each of the two branches of the apparatus 1, respectively referring to each of the two main conveyors 2a, 2b, has therefore a main loading/unloading station 5 at the same height as the respective main conveyor and an auxiliary loading/unloading station 50 arranged at a different height (overhead in the preferred embodiment, or underground in the embodiment shown in FIG. 13).

In the preferred embodiment the arrangement of the main and auxiliary stations 5,50 is perpendicular to the main direction of the two automatic conveyors 2a, 2b (FIG. 1). Nothing changes if, in an alternative embodiment, the main and auxiliary stations 5,50 are instead arranged parallel to the direction of the two main automatic conveyors 2a, 2b.

As previously indicated, the two auxiliary stations 50 of the two different branches of the apparatus 1 are connected by the auxiliary automatic conveyor 10, structurally similar to the two main conveyors 2a, 2b. Such auxiliary automatic conveyor 10 realizes the actual connection between the two distinct branches of the apparatus 1, allowing the bidirectional exchange of biological samples 3. It will be therefore appreciated that, in the shown example, the auxiliary conveyor 10 includes a pair of lanes 10a in order to perform a bidirectional transfer of biological samples 3.

The automation apparatus 1 comprises at least one central control unit E configured to control the transfer operations of the support devices 4 along the automation apparatus 1. The central electronic control unit E is configured to simultaneously control the handling of support devices 4 from the main conveyor 2a to the main conveyor 2b, passing through the auxiliary conveyor 10, and vice versa.

Preferably, each lift device 9 is controlled by a peripheral electronic control unit E1, E2 which coordinates the activities of the single lift device 9. Such peripheral electronic control units are configured to communicate with the central electronic control unit E.

In the case that the main automatic conveyors 2a, 2b realize two different branches of automation, without being connected to each other, the apparatus 1 includes two central electronic control units E which are configured to communicate with each other and with the peripheral electronic control units E1, E2, in order to coordinate the handling operations of the support devices 4.

Hereinafter, a detailed description on the use of the preferred embodiment of the apparatus according to the invention will be provided, referred as already mentioned to an overhead transfer of biological samples. However, such application is not to be intended in a limiting sense as the apparatus can also be used for a transfer of samples (between two branches connecting the same automation system or two different automation systems) that takes place underground.

In the use of the preferred embodiment, shown in FIGS. 3-10, the description is now limited to what happens along one of the two main conveyors 2a, 2b. Obviously, the discussion can be identically extended to the other main conveyor, in view of a bidirectional exchange of biological samples.

Considering the main conveyor 2b, it can be seen how at its end the support devices 4 (which may or may not house a test tube 3) transit in line on the main lane 11b and they are diverted if necessary to be addressed at the interface with the loading bay 6a of the main loading/unloading station 5. As previously indicated an interfacing lane 11d connects the main lane 11b to the loading bay 6a. The support devices 4 are deviated on the interfacing lane 11c by deviation mechanisms arranged in proximity to the lane. Such deviation mechanisms can be realized in accordance with what is described in the European patent EP 2780724 B1 by the same Applicant. The deviation mechanisms can include reading devices, in order to read an identification code of each support device 4 and of the related biological sample.

Figure 3:
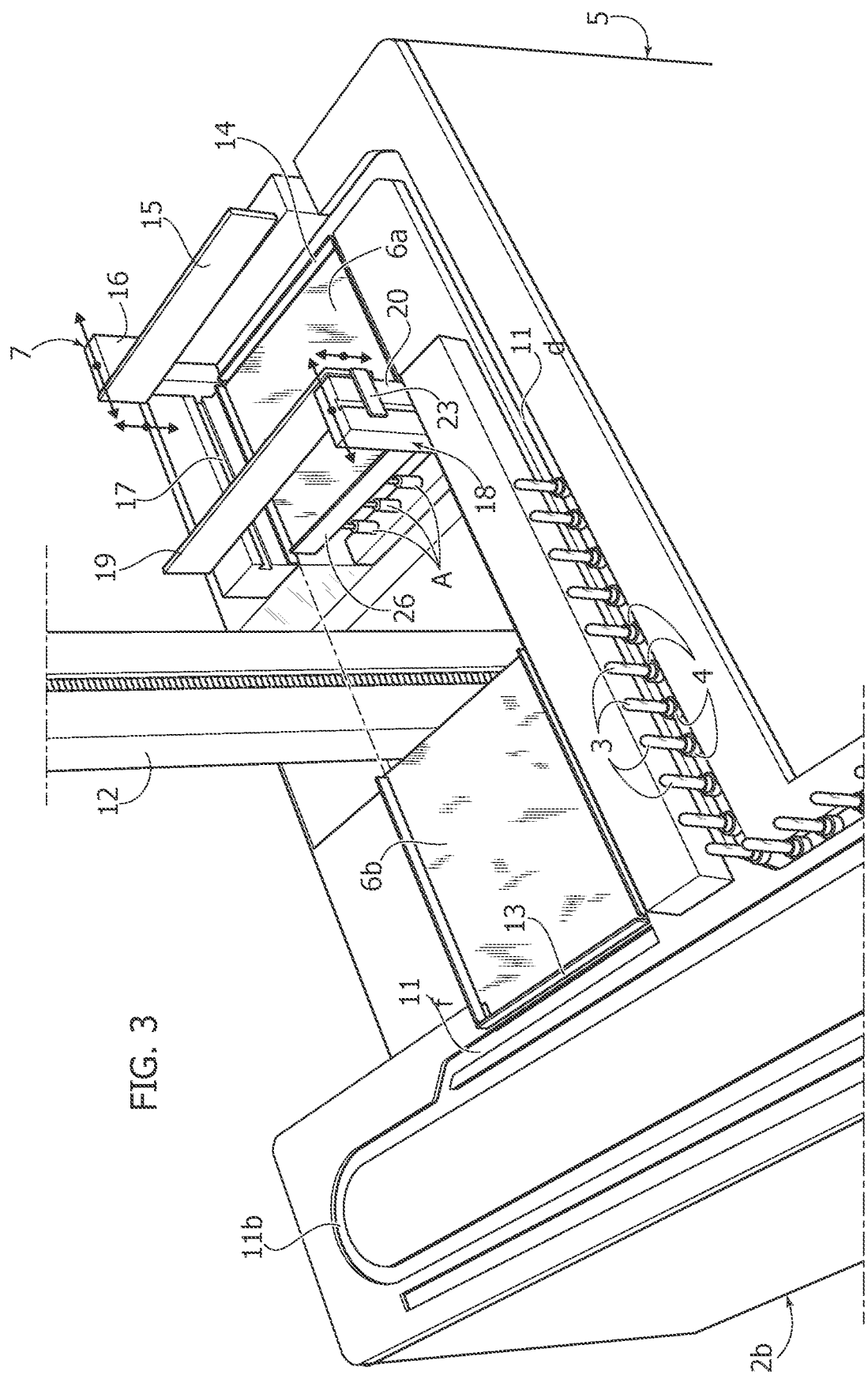

FIG. 3 illustrates a first working step in which a row of support devices 4 advances along the interfacing lane 11d, in the direction of the loading bay 6a. Preferably, the interfacing lane 11d includes a first section perpendicular to the main lane 11b and an end section parallel to the main lane 11b.

The loading bay 6a comprises respective handling elements configured to move rows of support devices 4 coming from the interfacing lane 11d. The handling elements of the loading bay 6a include a first pusher element 7 able to form batches of support devices 4 coming from the interfacing lane 11d, in particular from its end section, and to move the batches thus formed on the movable platform 8.

Figure 4:
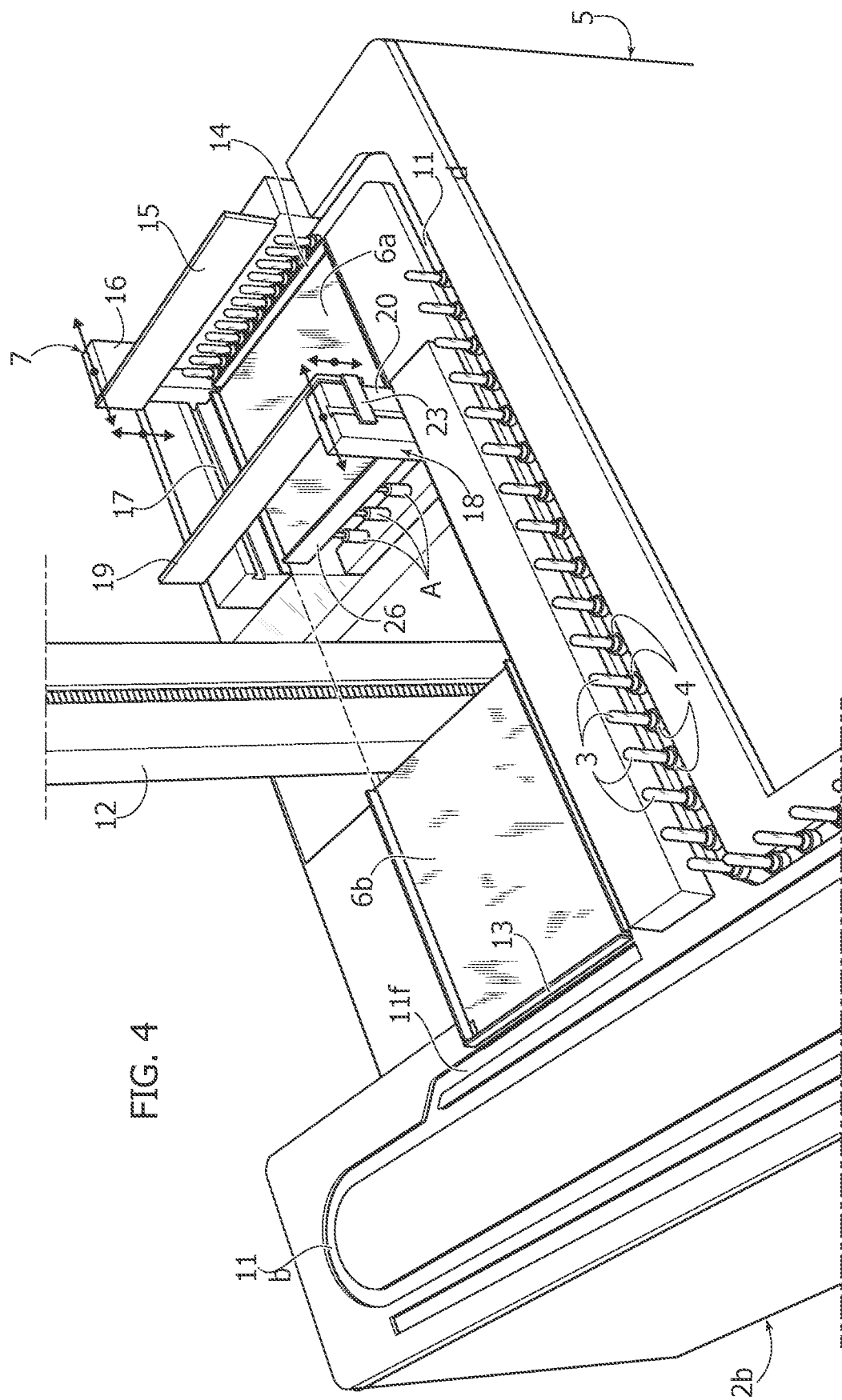

As shown in FIG. 4, when the support devices 4 end their path along the end section of the interfacing lane 11d, they are accumulated in line on the loading bay 6a, so as to fill the loading bay 6a in width.

Still with reference to the perspective view of FIG. 4, the handling elements of the loading bay 6a also include a first containment dividing wall 14, able to prevent the accidental advancement of the support devices 4 on the loading bay 6a, during the formation of the row on the end section of the interfacing lane 11d. Once a row consisting of a predetermined number of support devices 4 has been formed, filling the loading bay 6a in width, the first dividing wall 14 is controlled so as to lower into a slot arranged between the end section of the interfacing lane 11d and the bay 6a. The movement of the first dividing wall 14 is achieved by means of at least one actuator (not shown in the drawings). It will be therefore appreciated that following the lowering of the wall 14, the row of support devices 4 can advance on the loading bay 6a, in the direction of the movable platform 8, by means of the activation of the first pusher element 7.

Preferably the handling elements of the loading bay 6a also include a second containment dividing wall 26 arranged between the loading bay 6a and the movable platform 8, able to prevent the accidental advancement of the batch of support devices 4 on the movable platform 8, during the step of formation of the batch on the loading bay 6a. Such second dividing wall 26 is controlled by a series of actuators A, so as to lower when the batch is formed, in order to allow the transfer of the batch to the movable platform 8.

Figure 5:
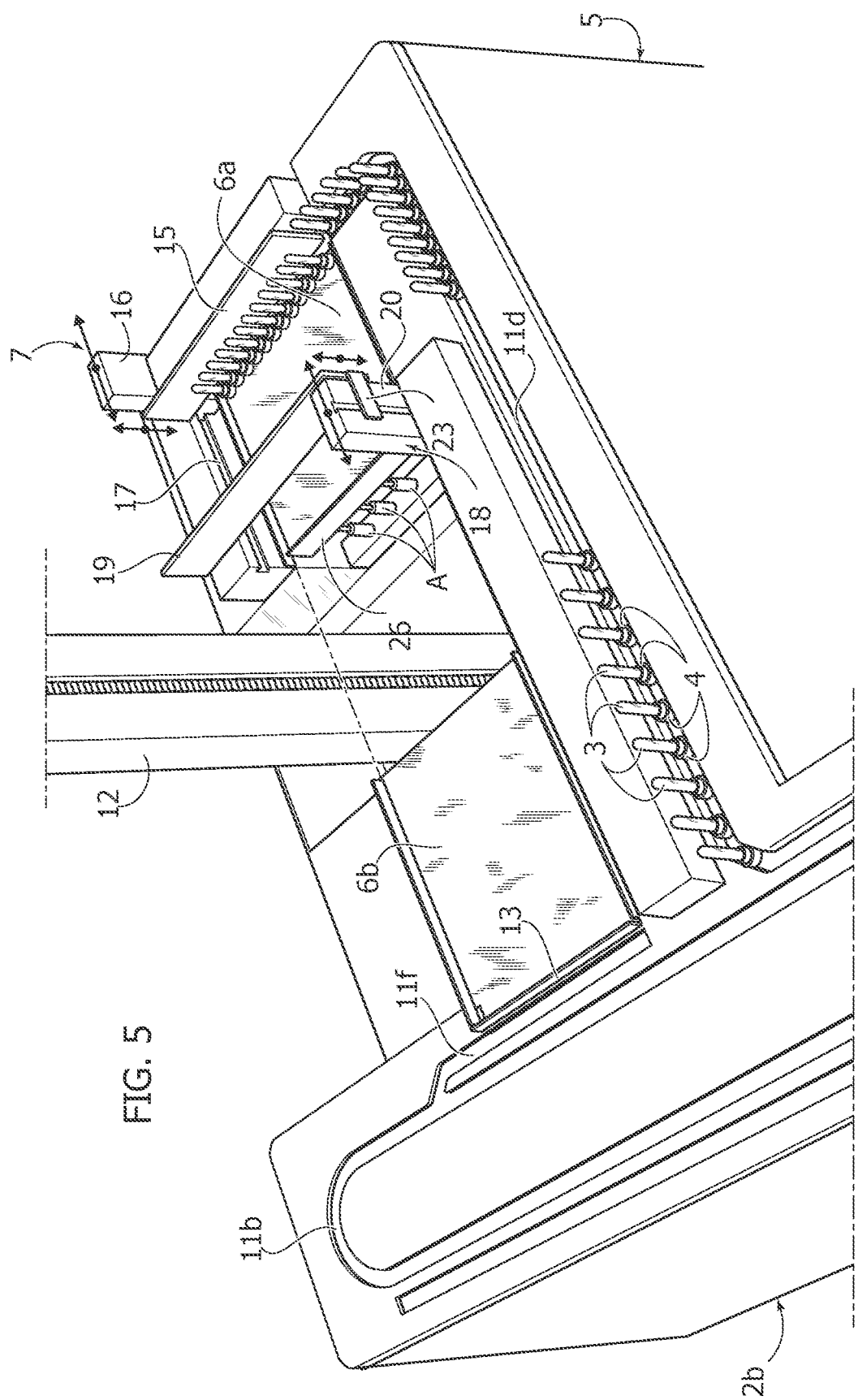
Figure 11:
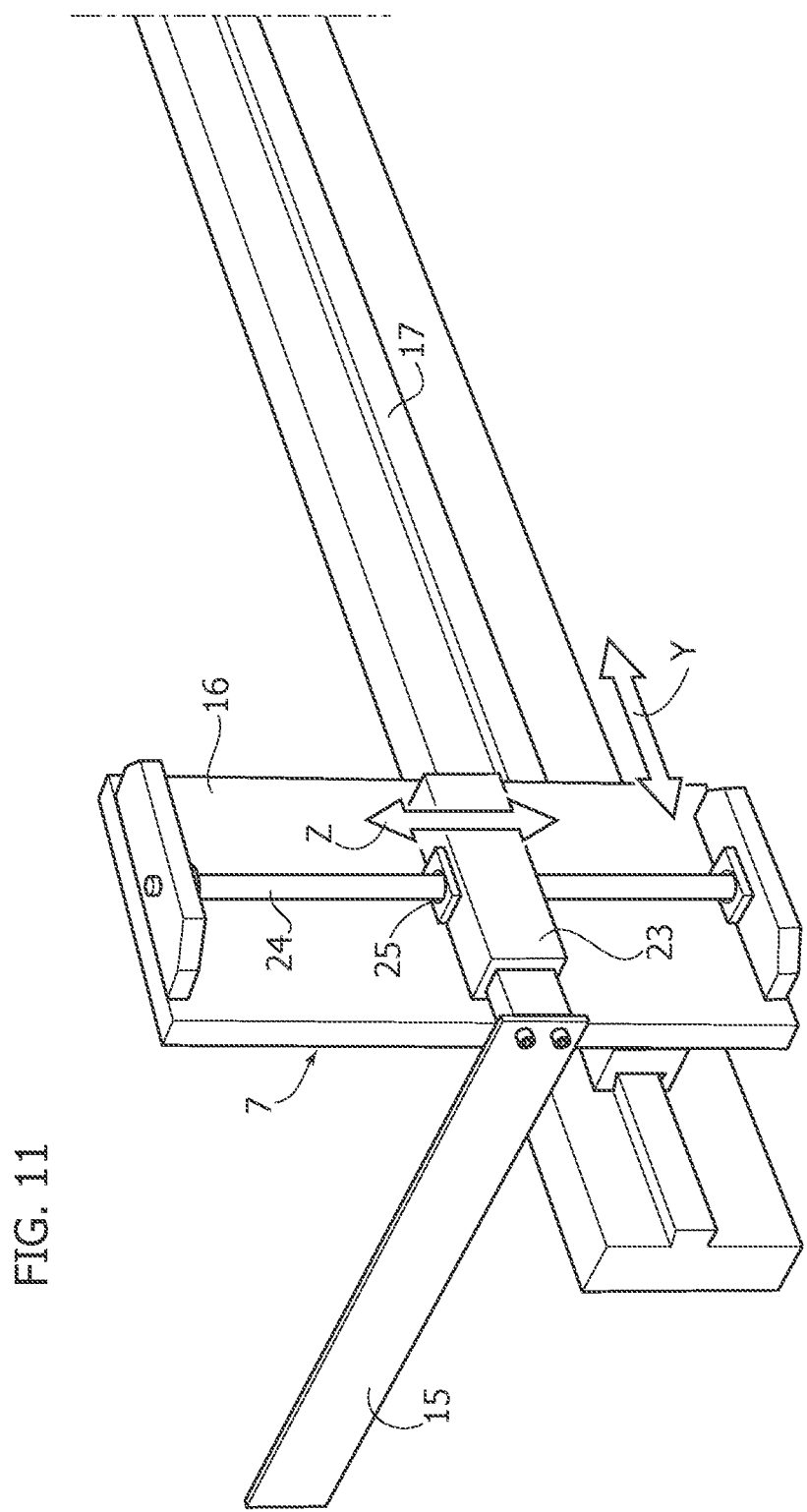
FIG. 11 is a schematic perspective view showing handling elements associated with a loading/unloading station.

According to a preferred embodiment, the first pusher element 7 includes a support structure 16 to which a horizontal bar element 15 is connected which extends transversely along the width of the loading bay 6a. As shown in the perspective view of FIG. 11, the support structure 16 is mounted sliding along respective guides 17 spaced along one side of the loading bay 6a opposite to a side of the bay 6a adjacent to the interfacing lane 11d. The bar 15 is supported by a support carriage 23 mounted vertically sliding along the support structure 16. It will be therefore appreciated that the first pusher element 7 is able to perform, during a working condition, a horizontal movement along a Y axis, toward/away from the movable platform 8, and a vertical movement along an axis Z, parallel to the direction of movement of the movable platform 8. In order to control the movement of the pusher elements 7, the stations 5, 50 are equipped with respective electric or fluid actuators. As illustrated in FIG. 11, the vertical movement of the carriage 23 is achieved by means of a vertical sliding of the carriage along a guide column 24 rigidly connected to the support structure 16. The connection portion of the carriage 23 to the guide column 24 comprises a bushing 25 made of a low-friction coefficient material. FIG. 5 illustrates a working step of the apparatus 1, in which the bar 15 of the first pusher element 7 is in the lowered configuration, to begin the pushing step on the bay 6a of one row of support devices 4.

As previously indicated, the horizontal bar 15 extends transversely along the width of the loading bay 6a and the support structure 16 is mounted sliding along the guides 17 and is controlled in order to slide along the length of the bay 6a in both directions. The guides 17 can be arranged facing the loading bay 6a (FIG. 2) or on the opposite side (FIG. 11).

Following the sliding of the support structure 16 along the guides 17, in the direction of the movable platform 8, the bar 15 which moves integrally with it, pushes the rows of support devices 4, in the direction of the movable platform 8. As previously indicated, the transverse bar 15 in its rest condition is in a spaced position with respect to the plane defined by the bay 6a and the first pusher element 7 also includes an actuator for guiding a vertical movement of the transverse bar 15, along the support structure 16 (in particular along the guide column 24). It will be therefore appreciated that the horizontal bar 15 can perform a vertical movement towards the bay 6a, before pushing the rows of support devices 4 towards the movable platform 8, so as to arrange itself at a suitable height for pushing the support devices 4 along the bay 6a. Once the pushing step along the plane of the bay 6a has been completed, the actuators drive the carriage 23 supporting the bar 15 to return to its raised rest condition, before making a horizontal movement of the support structure 16 along the guides 17, to return to the initial position.

Figure 6:
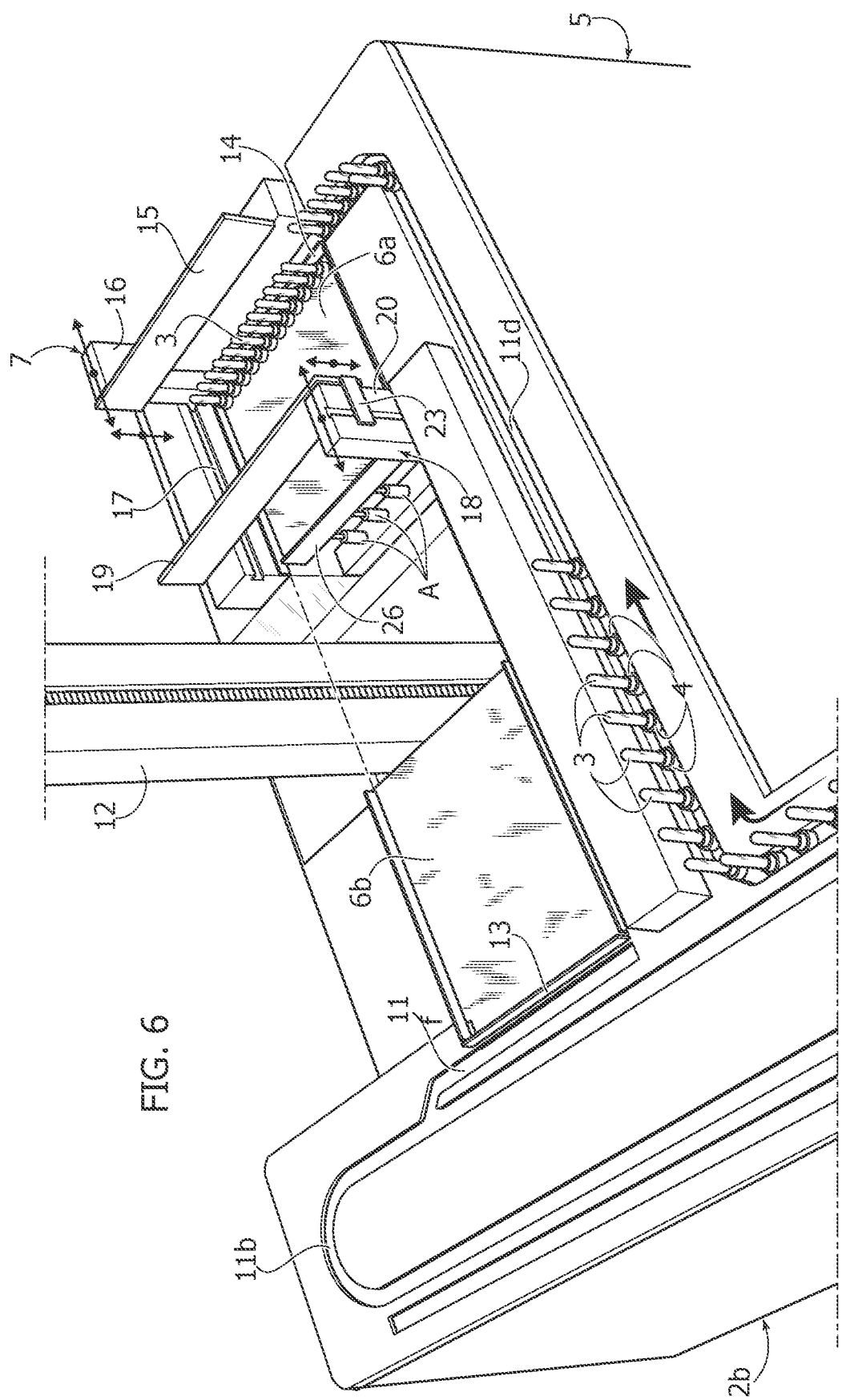

When, on the end section of the interfacing lane 11d, the accumulation of a predetermined number of support devices 4 capable of filling the width of the loading bay 6a is completed, the first pusher element 7 moves the aforementioned support devices 4 into the bay 6a, in the direction of the movable platform 8. The movement is carried out until leaving the necessary space for the arrangement of a next row of support devices 4 on the loading bay 6a, coming from the interfacing lane 11d. To perform the transfer on the bay 6a of the single row of support devices 4 coming from the interfacing lane 11d, the horizontal bar 15 moves from its raised rest configuration to a lowered working configuration. Afterwards, the support structure 16 bearing the carriage 23 and the horizontal bar 15 slides on the guides 17 in order to perform a movement along a horizontal direction towards the movable platform 8, and thus to push forward the row of support devices 4. The FIG. 6 illustrates the loading bay 6a in the condition in which the forward movement of a first row of support devices 4 on the loading bay 6a has just occurred. At this point the first pusher element returns to its initial rest configuration, waiting to push a second row of support devices 4 which meanwhile is forming on the end section of the interfacing lane 11d.

Figure 7:
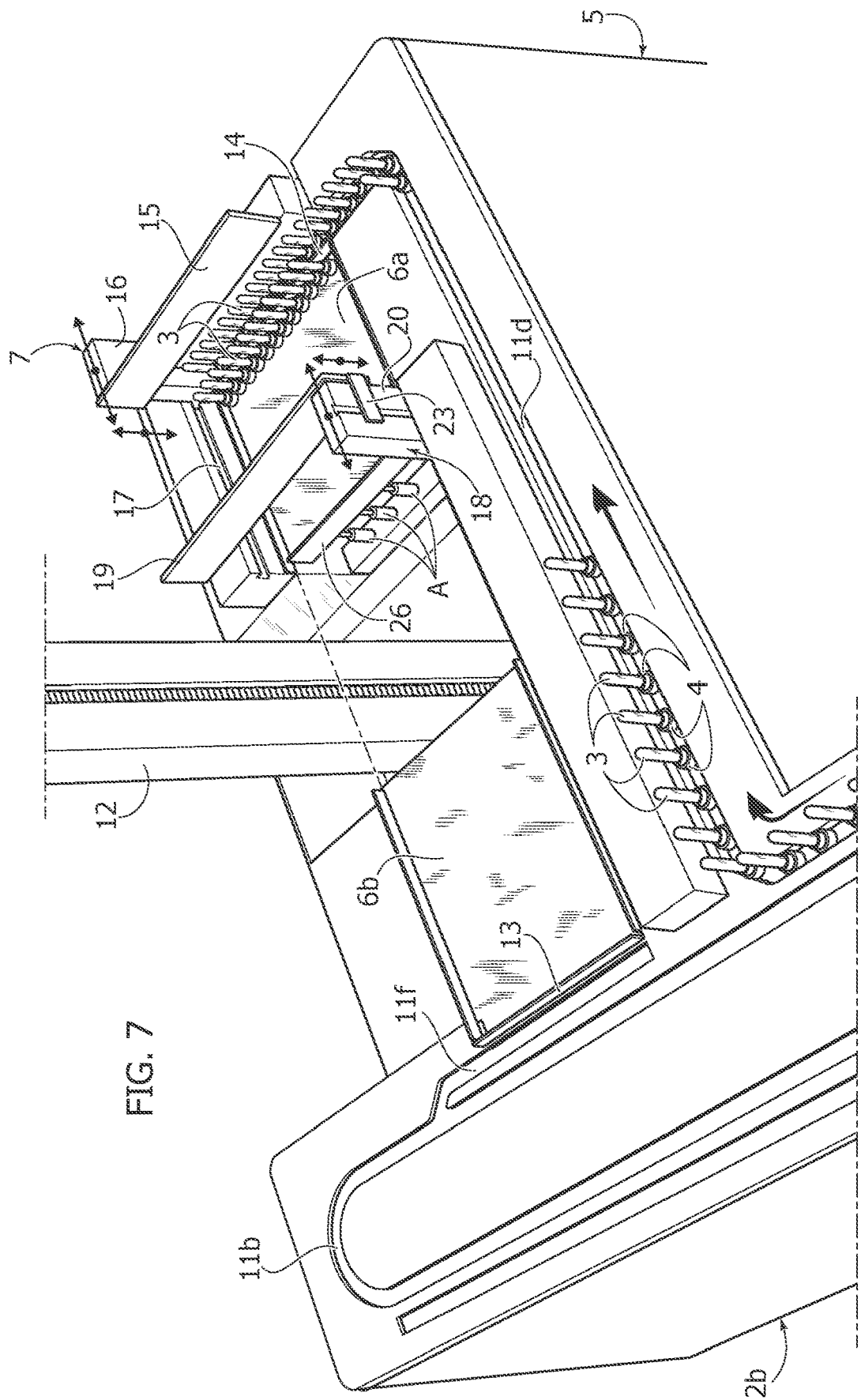
Figure 8:
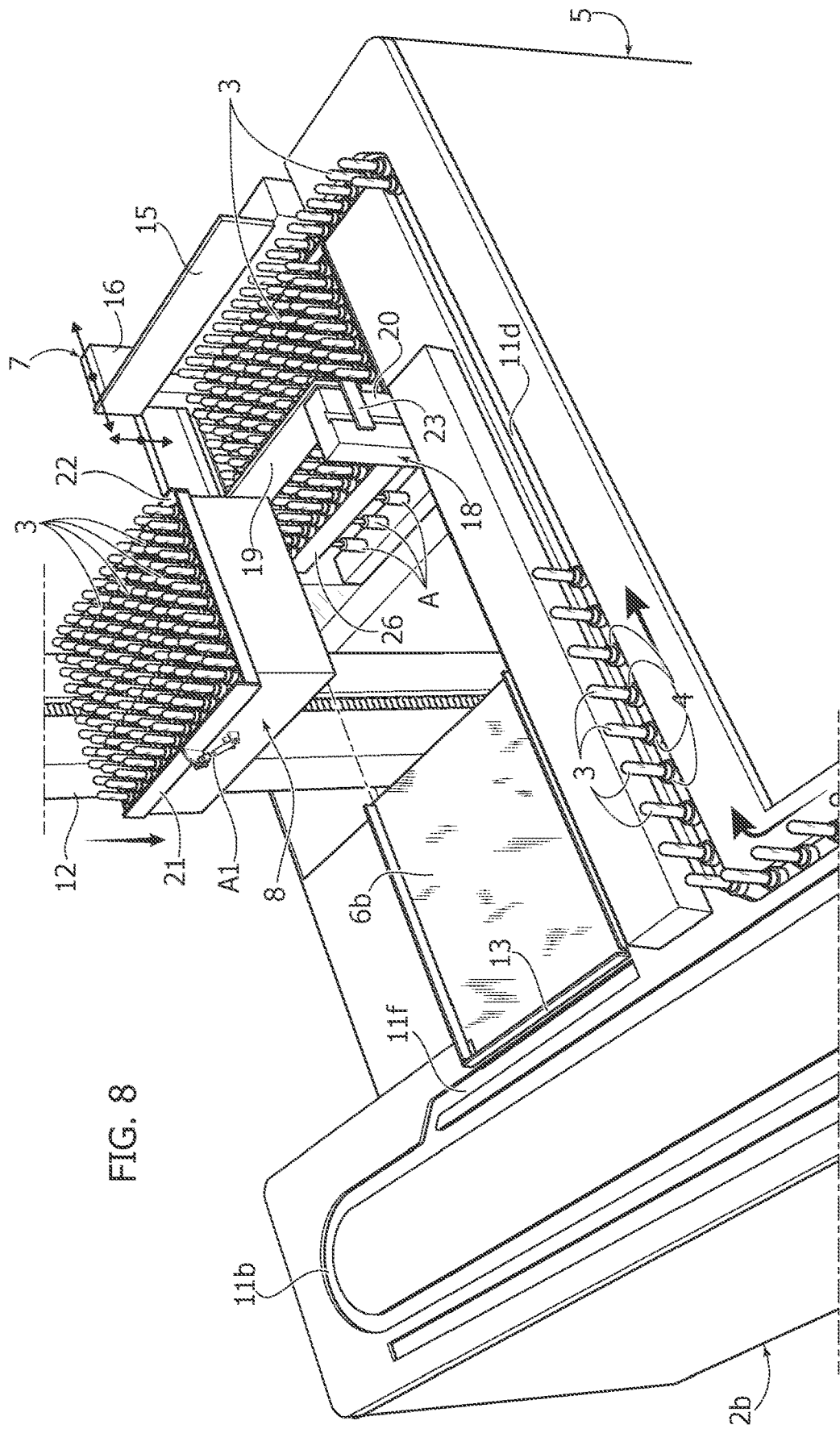

When a row of support devices 4 is pushed from the end section of the interfacing lane 11d onto the bay 6a, the first containment dividing wall 14 is arranged again in its raised configuration in order to reduce an accidental misalignment of a new row that is forming on the interfacing lane 11c (FIGS. 6-7). By repeating the operations above indicated for subsequent rows, the bay 6a is filled up since the rows previously loaded on the bay 6a are pushed towards the movable platform 8 every time a new row is loaded on the bay 6a. When, according to any known system (i.e., the use of sensors), the total filling of the loading bay 6a is distinguished, the second dividing wall 26 is lowered and the first pusher element 7 is activated to move the complete batch of devices support 4 from the loading bay 6a to the movable platform 8 of the lift device 9 (which in the meantime has arranged on the same plane as the loading bay 6a).

As previously indicated, the central electronic control unit E of the apparatus according to the invention is able to simultaneously control the handling of support devices 4 in two opposite directions. With reference in particular to the perspective view of FIG. 9, a working condition of the apparatus 1 is illustrated in which, near the completion of the loading step on the loading bay 6a, the movable platform 8 is controlled to move downwards transporting a batch of support devices 4 formed at the auxiliary station 50 above.

Figure 9:
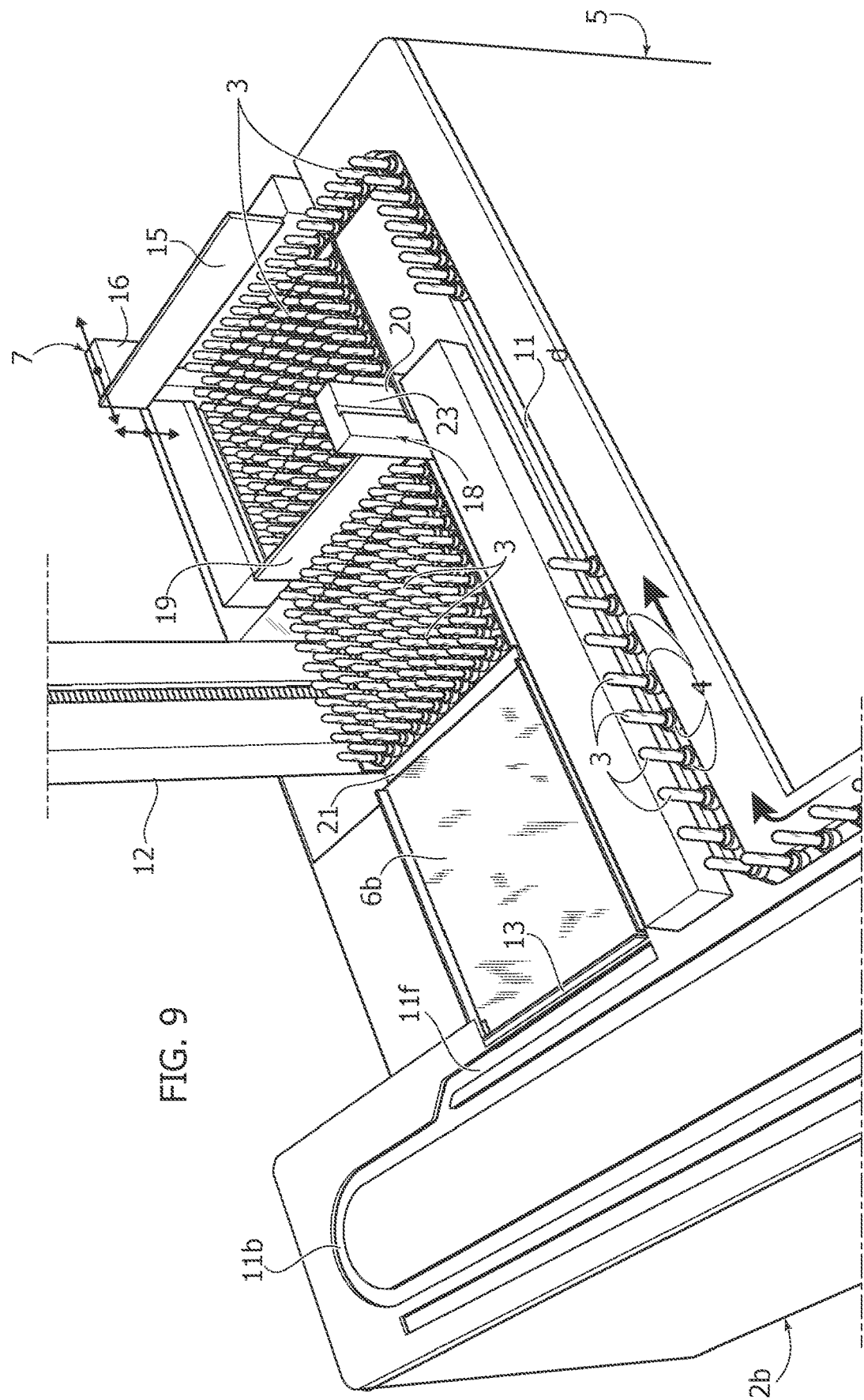

FIG. 9 illustrates a following working step, in which the movable platform 8 carrying the batch of support devices 4 reaches the plane of the main station 5. The lift devices 9 can include stroke end means associated with the movable platforms 8, so as to ensure perfect alignment of the movable platform 8 with the loading/unloading bays 6a, 6b. When the movable platform 8 reaches the plane of the main station 5, before proceeding with the loading of the batch of devices 4 formed on the loading bay 6a, the batch coming from the auxiliary conveyor 10 must be unloaded on the unloading bay 6b arranged on the opposite side with respect to the loading bay 6a.

Figure 10:
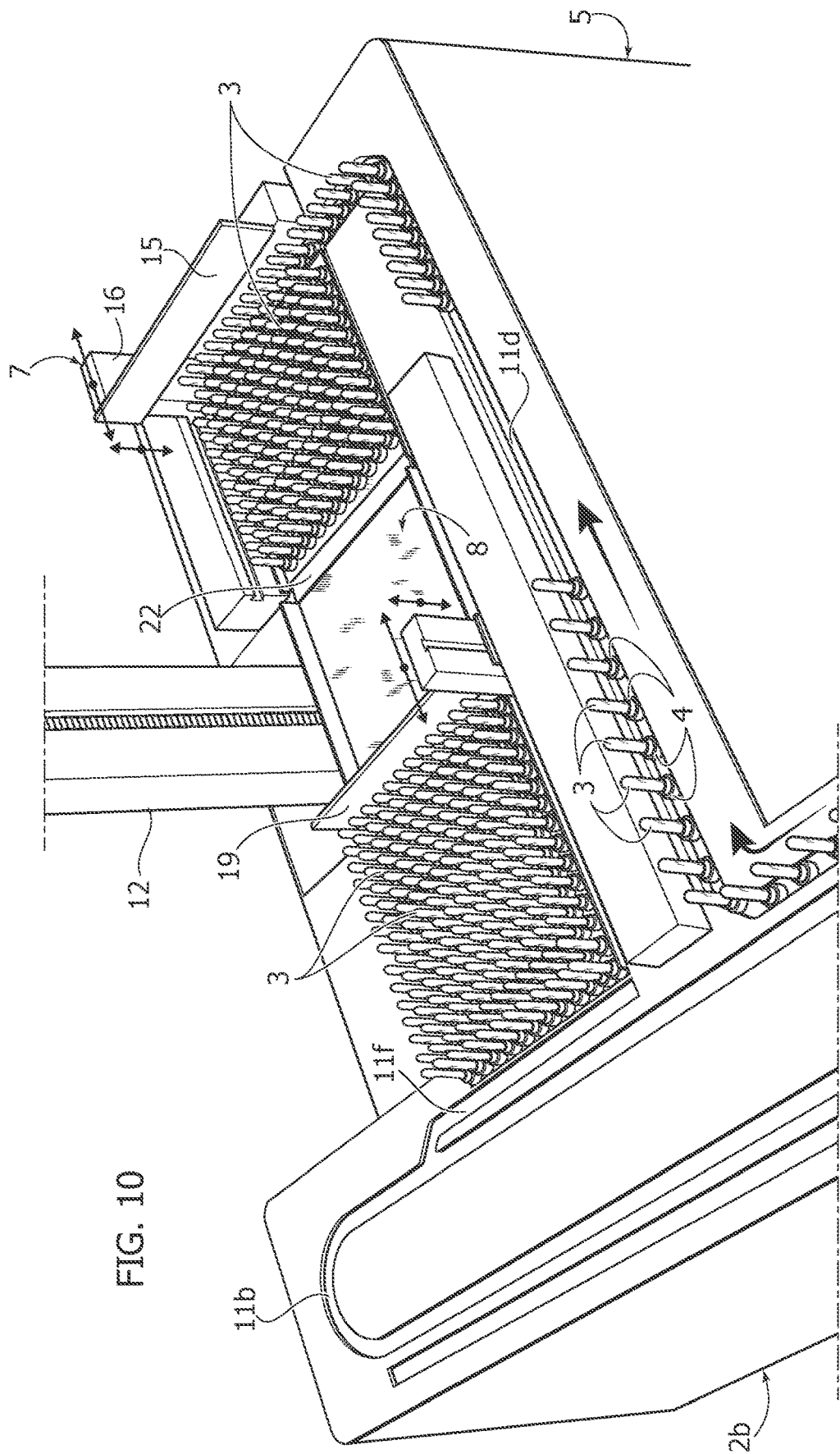

In order to perform the unloading step, the unloading bay 6b comprises a second pusher element 18 made in a completely similar way compared to the first pusher element 7. Thus, the second pusher element 18 includes a horizontal bar 19 carried by a support structure 20 mounted sliding along respective sliding guides. FIG. 10 illustrates a working unloading step, in which the second pusher element 18 pushes the batch of support devices 4 from the movable platform 8 to the automatic main conveyor 2b, passing through the unloading bay 6b. The ordered rows of support devices 4 are unloaded along a connecting lane 11f which connects the unloading bay 6b to the main lane 11b of the main conveyor 2b. Before proceeding with the unloading on the connecting lane 11f, a third dividing wall 13, arranged between the unloading bay 6b and such lane, must be lowered in a very similar way to what described for the walls 14, 26.

As shown in FIGS. 9-10, preferably the movable platform 8 includes along its sides adjacent to the loading and unloading bays 6a, 6b (when arranged on the same plane as the main station 5), respective connecting bridges 21, 22, able to create a continuous plane between the bays and the movable platform. When the movable platform 8 moves along the bearing structure of the respective lift device 9, such connecting bridges 21, 22 are configured as containment walls, so as to contain a batch present on the platform. When the movable platform 8 reaches the plane of the main station 5 or of the auxiliary station 50, the bridges rotate around a hinge axis, so as to create a continuous surface with the loading and unloading bays 6a, 6b. The connecting bridges 21, 22 are controlled by respective actuators A1 (partially illustrated in FIG. 8).

When a movable platform 8, carrying a batch loaded on the main station 5, reaches the respective auxiliary station 50, the batch is unloaded on the unloading bay 6b, again thanks to the action of a pusher, and each row of support devices 4 is sequentially released along the auxiliary conveyor 10.

The support devices 4 travel along the auxiliary conveyor 10 until reaching the other branch of the apparatus 1.

From here, according to a scheme specularly similar to what has already been described, they are directed towards the loading bay 6a of the auxiliary loading/unloading station 50 of the other branch, then loaded onto the platform 8 and carried, by the lift device 9, from the auxiliary station 50 to main station 5 at ground level. Finally, they are unloaded on the unloading bay 6b of the main station 5 and released along the main automatic conveyor 2a.

It is well understood how the management of the operations at the level of the entire apparatus 1 must ensure the parallelization between the two branches as well as the bidirectionality in the handling of the devices 4 and therefore of the biological samples 3.

Each of the two branches of the apparatus 1, just described according to a scheme that involves the ascent of devices 4 from the side where there is the conveyor 2a and the descent from the side of the conveyor 2b, can certainly operate in the opposite direction.

On the other hand, since each of the two lift devices 9 can operate alternatively with only one of the two ascent or descent movements, it is necessary to properly coordinate all the devices involved to avoid conflicts between the aforementioned two operating modes.

The apparatus 1 is managed by the peripheral control units E1 and E2 with the supervision of at least one central control unit E.

In other words, the working routine between two distinct loading/unloading stations 5 and 50 of the same branch of the apparatus 1 provides for the loading of support devices 4 from the automatic conveyor (whether it is one of the main 2a or 2b or the auxiliary 10 depending on whether it is the main station 5 or the auxiliary 50) towards the lift device 9, and later the unloading of the support devices 4 just received from the other station through the lift device 9 and their release towards the automatic conveyor. Everything takes place according to a suitable exchange of information between the two stations 5, 50 of the same branch, in order to be able to properly share the use of the lift device 9.

In accordance with the embodiment of FIGS. 1, 13, the overall working routine of the apparatus 1 arises from the interaction between the working routines of the four single loading/unloading stations (two 5 and two 50) present, grouped at the firmware level into two distinct control instances.

Each control instance referred to one of the two branches of the apparatus 1 acts independently from the other, in the context of the management of the activities limited to the branch itself. A communication between the two control instances is necessary in relation to the information that the two branches must exchange in order to be able to appropriately share the auxiliary conveyor 10 without conflicts.

The shared information includes, although not being limited to:
- the working status of each of the two branches (whether online or offline);
- the presence of errors which block one of the devices along a branch;
- the situation of loading of an entire batch of support devices 4 from the auxiliary conveyor 10 to one of the two stations 50, notified by the branch in which such loading took place in order to allow also the other branch to update the count of the support devices 4 present on the auxiliary conveyor 10.

In general, the apparatus 1 always keeps track through the central control unit E of the number of support devices 4 present in each of its stations to avoid conflicts, traffic jams and to detect eventual transport devices 4 improperly blocked and therefore unable to leave a specific area of the apparatus 1 as instead expected.

In a preferred embodiment, all these information are saved in a file in order to be recovered in the unfortunate case of a sudden block of the apparatus 1.

In this case, during the re-initialization step of the apparatus 1, it checks whether the information related to the number of support devices 4 in each station, or along the auxiliary conveyor 10, are still valid. If this is not the case, or if it was not possible to save any information, a rough estimate of such number is performed in order to continue to operate safely.

Finally it should be borne in mind that both support devices 4 with test tube 3 and empty support devices 4 can of course circulate inside the same apparatus 1, and be simultaneously moved, in order to ensure a balance of the aforementioned types between the two distinct branches of the apparatus 1 and according to the operating volumes required by the processing or analysis modules of biological samples placed in interface with the main conveyors 2a and 2b.

Figure 12:
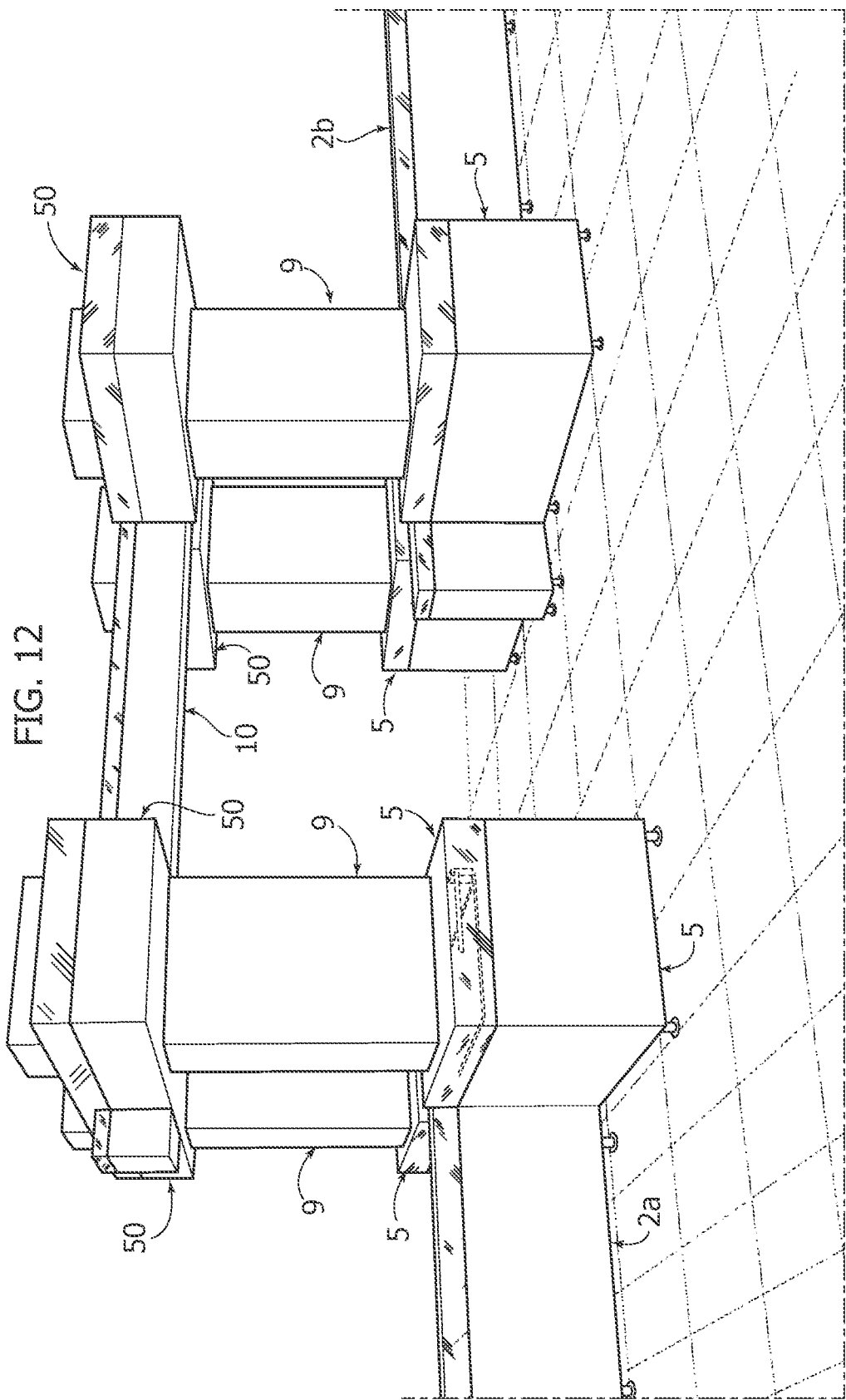
FIGS. 12, 13 are perspective views of an automation apparatus of analysis laboratory, respectively according to further embodiments of the invention.

In accordance with the embodiment illustrated in FIG. 12, each branch of the apparatus can include a pair of lift devices 9, in which each lift device 9 is associated respectively with a pair of main/auxiliary stations 5,50. In order to increase the transfer rate of samples along the system, more than two lift devices for each branch of the apparatus can also be provided.

As is evident from the foregoing description, the apparatus according to the invention allows to move part of a laboratory automation system to a different level, in height, compared to that represented by the floor of the laboratory itself, allowing a reduction of the area occupied by the laboratory automation system and therefore a minor hindrance to the passage of laboratory personnel and to the transport of objects, without however affecting the throughput of handled samples.

Moreover, it is well understood how the distance that a single sample circulating along the automation system must cover in order to pass from a given processing or analysis module to another can be reduced.

Furthermore, the solution is identically applicable to connect two distinct portions of the same automation system, but also two distinct automation systems located in the same analysis laboratory.

The apparatus according to the invention also allows to obviate in this way to any type of breakdown or failure that occurs temporarily in a portion of an automation system, which makes one or more of the related processing or analysis modules unavailable, by suitably and in a short time transferring the samples to other portions of the same automation system or to another automation system.

Finally, the illustrated solution is totally modular and scalable, showing total adaptability to any throughput required in the laboratory, as well as to laboratories of any size.

Studies and experiences performed by the Applicant have shown that the use of an apparatus such as that described in the present invention allows, compared to currently known devices, a considerable saving of time and resources in the context of pre-analysis, analysis and post-analysis activities carried out in the laboratory.

Of course, without prejudice to the principle of the invention, the construction details and the embodiments may vary widely with respect to what is described and illustrated purely by way of example, without thereby departing from the scope of protection of the present invention, as defined in the annexed claims.

What is claimed is:

1. An automation apparatus of an analysis laboratory, for handling support devices which support a single container of biological samples, said automation apparatus comprising:
   two main automatic belt conveyors arranged in positions spaced apart from one another on a floor, and having at least one respective main guide lane on which the support devices are configured to run,
   at least two lift devices, each associated with a respective main automatic belt conveyor and each including a bearing structure spaced in a substantially vertical direction, and a movable platform carried by said bearing structure and arranged movable along said bearing structure,
   at least two main loading/unloading stations, each associated with a respective one of the two main automatic belt conveyors and a respective one of the two lift devices thereof, each main station being configured to form and temporarily host batches of said support devices coming from the respective main guide lane, said batches being formed to be transferred to the respective movable platform, or vice versa,
   at least one auxiliary automatic belt conveyor having at least one auxiliary transport lane, on which the support devices are configured to run, said auxiliary automatic conveyor being operatively connected to the main automatic belt conveyors by means of the lift devices, and being spaced at a different height with respect to said main automatic belt conveyors, so that said auxiliary automatic belt conveyor is configured to allow a transport flow of the support devices from one main automatic belt conveyor to the other main automatic belt conveyor and/or vice versa, while space between the spaced apart two automatic belt conveyors is configured to allow passage of human operators between the two main automatic belt conveyors from one longitudinal side of both of the two automatic belt conveyors to the other longitudinal side of both of the two main automatic belt conveyors by underpassing or overpassing the auxiliary automatic belt conveyor, wherein the auxiliary automatic belt conveyor is configured to be positioned in one of i) a first position raised above the two main belt conveyors configured to facilitate the human operator underpassing, and ii) a second position lowered below the two main automatic belt conveyors configured to facilitate the human operator overpassing, at least a pair of auxiliary loading/unloading stations located at a same height as the auxiliary automatic belt conveyor, each auxiliary station being associated with a respective lift device and being configured to form and host batches of said support devices coming from the auxiliary transport lane, said batches being formed to be transferred to the respective movable platform, or vice versa, each main and auxiliary loading/unloading station including respective handling elements configured to form batches of support devices and to carry out a loading step of said batches on the movable platform and/or an unloading step of said batches from the movable platform, said automation apparatus further comprising at least one central electronic control unit configured to control handling operations of the support devices along the main and auxiliary belt conveyors.

2. The automation apparatus according to claim 1, wherein said central electronic control unit is configured to simultaneously control transfer of support devices from the main automatic belt conveyors to the auxiliary automatic belt conveyor, and vice versa.

3. The automation apparatus, according to claim 1, wherein the main and auxiliary automatic belt conveyors include respective interfacing lanes which connect the main/auxiliary lanes to the respective main/auxiliary station located at the same height, the interfacing lanes of the main automatic belt conveyors being arranged downstream of deviation mechanisms arranged on the respective main lanes, configured to divert a path of some support devices from the main lanes to the main stations.

4. The automation apparatus according to claim 1, wherein each main and auxiliary loading/unloading station comprises a loading bay and an unloading bay, arranged on two opposite sides of the respective movable platform, said loading and unloading bays including, respectively, a set of said handling elements.

5. The automation apparatus according to claim 4, wherein the handling elements of each loading bay include a first pusher element configured to form batches of support devices coming from a respective interfacing lane and to move said batches on the respective movable platform.

6. The automation apparatus according to claim 5, wherein said first pusher element is configured to push ahead on the loading bay a row of support devices coming from the interfacing lane, in a direction of the movable platform, said first pusher element being further configured to repeat a shift operation for following rows until filling the loading bay, and to move a batch of support devices formed as a result of a shift of multiple rows, from the loading bay to the movable platform.

7. The automation apparatus according to claim 5, wherein said first pusher element includes a support structure to which a horizontal bar element is connected which extends transversely along a width of the loading bay, said support structure being mounted sliding along respective guides spaced along one side of the loading bay, and said horizontal bar element being mounted vertically sliding along the support structure.

8. The automation apparatus according to claim 4, wherein the handling elements of each loading bay further include a first containment dividing wall, arranged between an end section of an interfacing lane and the respective loading bay, said first containment dividing wall being controlled so as to lower when a row of support devices is formed on said end section, in order to prevent an accidental advancement of the support devices in a direction of the movable platform and to allow transfer of a row of support devices from the interfacing lane to the loading bay.

9. The automation apparatus according to claim 4, wherein each movable platform includes along its adjacent sides, respectively at the loading bays and at the unloading bays, respective movable connecting bridges, configured to create a continuous plane between the loading and unloading bays and the movable platform when the movable platform reaches a level of a main or auxiliary loading/unloading station, and to create containment walls during steps of ascent and descent of the movable platform along the bearing structures of the lift devices.

10. The automation apparatus according to claim 4, wherein the handling elements of the unloading bays include a second pusher element configured to move a batch of support devices from the movable platform to the main/auxiliary lane, temporarily passing through the unloading bay.

11. The automation apparatus according to claim 4, wherein the main/auxiliary loading/unloading stations include respective sensor means to discriminate a complete filling of the loading bay and to activate the handling elements of said loading bay.

12. An automation system including a plurality of apparatuses according to claim 1, said apparatuses being operatively connected to each other.

* * * * *